US005811239A

United States Patent [19]

Frayne

[11] Patent Number: 5,811,239

[45] Date of Patent: Sep. 22, 1998

[54] METHOD FOR SINGLE BASE-PAIR DNA SEQUENCE VARIATION DETECTION

[75] Inventor: Elizabeth Gay Frayne, Diamond Bar, Calif.

[73] Assignee: Frayne Consultants, Diamond Bar, Calif.

[21] Appl. No.: 645,600

[22] Filed: May 13, 1996

Related U.S. Application Data

[60] Provisional application No. 60/007,807 Nov. 30, 1995.

[51] Int. Cl.[6] .............................. C12Q 1/68; C12Q 1/04; C12N 15/01

[52] U.S. Cl. .................................... 435/6; 435/5; 435/34; 435/172.1; 435/172.3; 435/820

[58] Field of Search ......................... 435/6, 172.1, 172.3, 435/5, 34, 820

[56] References Cited

U.S. PATENT DOCUMENTS

| | | | |
|---|---|---|---|
| 4,683,202 | 7/1987 | Mullis | 435/91.2 |
| 5,075,217 | 12/1991 | Webor | 435/6 |
| 5,126,239 | 6/1992 | Livak | 435/6 |
| 5,192,659 | 3/1993 | Simons | 435/6 |

FOREIGN PATENT DOCUMENTS

| | | |
|---|---|---|
| 91/15600 | 10/1991 | WIPO . |
| 93/08297 | 4/1993 | WIPO . |
| 94/20641 | 9/1994 | WIPO . |

OTHER PUBLICATIONS

Ma et al., "Improved Quantification w/ Validation of Multiple mRNA Species by Polymerase Chain Reaction" Cardiovascular Res. vol. 28 464–471, 1994.

Sugano et al. "Rapid & Simple Detection of c–ki–ras 2 Gene Coding Mutations . . . " Lab. Invest. 68(3) 361–366, 1993.

Limon et al. "Presentation of a PCD–Nuclease Protection Strategy . . . " Leukemia 9 656–661, 1995.

Tanaka–Yamamoto et al. "Specific Amplification of Deleted Mitochondrial DNA from a Myopathic Patient . . . " 1009 151–155 Biochim Biophys Acta, 1989.

Shenk et al Biochemical Method for Mapping Mutational PNAS Alterations in DNA with Sl Nuclease: The Location of Deletions & TS Mutations in SU40 vol. 72 989–993, 1975.

Dodgson & Wells Action of Single–Strand Specific Nucleases on Model DNA Heteroduplexes of Defined Size & Sequence Biochemistry vol. 16 2374–2379, 1977.

Meyers et al Detection of Single Base Substitutions in Total Genomic DNA Nature vol. 313 495–496, 1985.

Mashal et al "Detection of Mutations by Cleavase of DNA Heteroduplexes with Bacteriophage Resoluases" Nature Genetics vol. 9 180 (177–183), 1995.

Yovil et al "Screening for Mutations by Enzyme Mismatch Cleavase with T4 Endonuclease" PNAS vol. 92 87–91, 1995.

Eng & Vijg "Genetic Testing: The Problems and the Promis" in Nature Biotechnology vol. 15 422–426, 1997.

Wagner et al "Mutation Detection Using Immobilized Mismatch Binding Protein (MUTS)" Nucleic Acids Res. vol. 23 3944–3948, 1995.

Genecheck Trade Literature Indicating Size Dependence 100–300 Base Pairs for Muts 400 E. Horsetooth Fort Collins CO 80525, 1996.

Meyers et al "Detection of Single Base Substitutions by Ribonuclease Cleavage at Mismatches in RNA:DNA Duplexes" Science vol. 230 1242–1246, 1985.

Hofker et al The X Chromosome Shows Less Genetic Variation at Restriction Sites than the Autosomes Am J. Hum. Genet. vol. 39:438–437, 1986.

Rowen et al "The Complete 685–Kilobase DNA Sequence of the Human BT Cell Receptor Locus" Science 272: 1755–1762, 1996.

Risch "Linkage Strategies for Genetically Complex Traits, II The Power of Affected Relative Pairs" Am J. Hum. Genetics 46: 229–241, 1990.

Risch Linkage Strategies for Genetically Complex Traits. III The Effect of Marker of Affected Relative Pairs Polymorphism or Analysis Am J. Hum. Genetic 46:242–253, 1990.

Risch & Merikanses "The Future of Genetic Studies of Complex Human Diseases" Science 273:1516–1517, 1996.

Scott et al., Bell & Taylor; Long et al; Muller–Myhsok & Abel; Risch & Merikangas Science 275:1327–1330, 1997. "Genetic Analysis of Complex Diseases".

Roberts et al "Detection of Novel Genetic Markers by Mismatch Analysis" Nuc. Acids Res. vol. 17 5961–71, 1989.

Wang et al Toward a Third Generation Genetic Map at the Human Genome Based on Bi–Allelic Polymorphisms Society of Human Genetics 46th Conference Abstract A3:4, 1996.

Research Genetics Trade Literature Pertaining to Heterozygosity of Microsatellites.

Berk & Sharp "Sizing & Mapping of Early Cell Adenovirus mRNAs by Gel Electrophoresis of SI Endonuclease–Digested Htbrids" vol. 12:721–731, 1977.

*Primary Examiner*—Nancy Degen

[57] ABSTRACT

The present invention describes a method for the detection of single base-pair DNA sequence variation in DNA samples isolated from cells with limited ploidy (1~3N). The method can detect variation essentially anywhere in the genome. The method comprises identifying single base-pair polymorphisms or mutations by amplifying a specific region of genomic DNA using a polymerase chain reaction, denaturation of the resultant chains followed by renaturation to form a heteroduplex or hybrid DNA molecule containing one or more single base-pair mismatches. The heteroduplex is then digested with S1 nuclease and the products separated by size with detection by Southern Blot, the use of labeled primers or sensitive gel staining. The method should be generally useful as a simplified approach to identify DNA sequence variants in a variety of samples. It also provides a potentially powerful approach to genetic mapping, DNA fingerprinting, disease detection, and population genetics.

15 Claims, 1 Drawing Sheet

Figure 1(A)

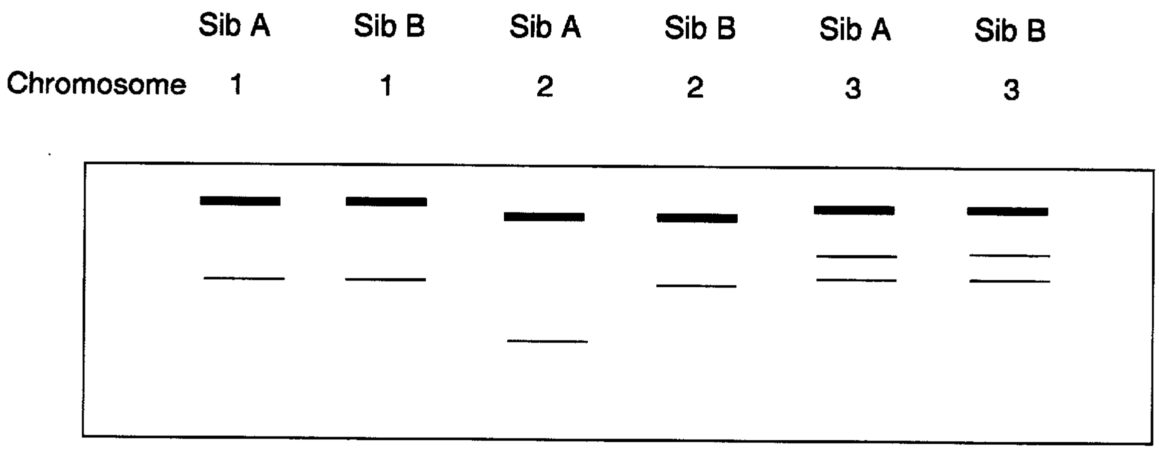

Comparison of Affected Siblings for Homozygous Recessive Condition
Bands are indicated as full-length : ▬▬ or S1 digestion product : ——.
Chromosome 1 & 3 are potential candidates by virtue of an identical banding pattern.

Figure 1(B)

Comparison of Affected Relatives for a Dominant Condition
Chromosome one is a candidate by virtue of one band shared in common among all. Other bands from digestion correspond to unrelated alleles.

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 23 bp
( B ) TYPE: nucleic acid
( C ) STRANDEDNESS: single
( D ) TOPOLOGY: linear ( i i ) MOLECULE TYPE: genomic DNA
( A ) DESCRIPTION: upstream PCR primer for p53 gene spanning the 5'exon/intron junction for exon five ( i i i ) HYPOTHETICAL: no ( i v ) ANTI-SENSE: no ( v i ) ORIGINAL SOURCE:
( A ) ORGANISM: homo sapien
( B ) TISSUE TYPE: placenta ( v i i i ) POSITION IN GENOME:
( A ) CHROMOSOME/SEGMENT: 17p13

( x ) PUBLICATION INFORMATION:
( A ) AUTHORS: Buchman, V. L., Chumakov, P. M., Ninkina, N. N., Samarina, O. P. and Georgiev, G. P.
( B ) TITLE: A variation in the structure of the protein-coding region of the human p53 gene
( C ) JOURNAL: Gene
( D ) VOLUME: 70
( E ) PAGES: 245-252
( F ) DATE: 1988
( G ) RELEVANT RESIDUES IN SEQ ID NO: 1: 1-23

( x i ) SEQUENCE DESCRIPTION: SEQ ID NO: 1:

CTCTTCCTGC AG TAC TCC CCT GC 23

( 2 ) INFORMATION FOR SEQ ID NO: 2:

( i ) SEQUENCE CHARACTERISTICS:
( A ) LENGTH: 24 bp
( B ) TYPE: nucleic acid
( C ) STRANDEDNESS: single
( D ) TOPOLOGY: linear ( i i ) MOLECULE TYPE: genomic DNA
( A ) DESCRIPTION: downstream PCR primer for p53 gene spanning the 3'exon/intron boundary for exon six ( i i i ) HYPOTHETICAL: no ( i v ) ANTI-SENSE: yes ( v ) ORIGINAL SOURCE:

( A ) ORGANISM: homo sapien
( B ) TISSUE TYPE: placenta ( v i i i ) POSITION IN GENOME:
( A ) CHROMOSOME/SEGMENT: 17p13

( x ) PUBLICATION INFORMATION:
( A ) AUTHORS: Buchman, V. L., Chumakov, P. M., Ninkina, N. N., Samarina, O. P. and Georgiev, G. P.
( B ) TITLE: A variation in the structure of the protein-coding region of the human p53 gene
( C ) JOURNAL: Gene
( D ) VOLUME: 70
( E ) PAGES: 245-252
( F ) DATE: 1988
( G ) RELEVANT RESIDUES IN SEQ ID NO: 2: 1-24

( x i ) SEQUENCE DESCRIPTION: SEQ ID NO: 2:

GGCCACTGAC AACCACCCTT AACC 24

( 2 ) INFORMATION FOR SEQ ID NO: 3:

( i ) SEQUENCE CHARACTERISTICS:
( A ) LENGTH: 24 bp
( B ) TYPE: nucleic acid
( C ) STRANDEDNESS: single
( D ) TOPOLOGY: linear ( i i ) MOLECULE TYPE: genomic DNA
( A ) DESCRIPTION: upstream PCR primer for p53 gene spanning the 5'exon/intron boundary for exon seven ( i i i ) HYPOTHETICAL: no ( i v ) ANTI-SENSE: no ( v i ) ORIGINAL SOURCE:
( A ) ORGANISM: homo sapien ( v i i ) IMMEDIATE SOURCE:
( A ) LIBRARY: EMBL/GeneBank/DDBJ databases, accession # X54156

( v i i i ) POSITION IN GENOME:
( A ) CHROMOSOME/SEGMENT: 17p13

( x ) PUBLICATION INFORMATION:
( A ) AUTHORS: Chumakov, P. M.
( B ) TITLE: Human p53 gene for transformation related protein p53
( F ) DATE: 1990
( G ) RELEVANT RESIDUES IN SEQ ID NO: 3: 1-24

( x i ) SEQUENCE DESCRIPTION: SEQ ID NO: 3:

GTGTTGTCTC CTAG GTT GGC TCT G 24

( 2 ) INFORMATION FOR SEQ ID NO: 4:

( i ) SEQUENCE CHARACTERISTICS:
( A ) LENGTH: 24 bp
( B ) TYPE: nucleic acid
( C ) STRANDEDNESS: single
( D ) TOPOLOGY: linear ( i i ) MOLECULE TYPE: genomic DNA
( A ) DESCRIPTION: downstream PCR primer for p53 gene spanning the 3'exon/intron boundary for exon eight ( i i i ) HYPOTHETICAL: no ( i v ) ANTI-SENSE: yes ( v i ) ORIGINAL SOURCE:
( A ) ORGANISM: homo sapien
( B ) TISSUE TYPE: placenta -continued ( v i i i ) POSITION IN GENOME:
( A ) CHROMOSOME/SEGMENT: 17p13

( x ) PUBLICATION INFORMATION:
( A ) AUTHORS: Buchman, V. L., Chumakov, P. M., Ninkina, N. N., Samarina, O. P. and Georgiev, G. P.
( B ) TITLE: A variation in the structure of the protein-coding region of the human p53 gene
( C ) JOURNAL: Gene
( D ) VOLUME: 70
( E ) PAGES: 245-252
( F ) DATE: 1988
( G ) RELEVANT RESIDUES IN SEQ ID NO: 4: 1-24

( x i ) SEQUENCE DESCRIPTION: SEQ ID NO: 4:

GTCCTGCTTG CTTAC C TCG CTT AG 24

METHOD FOR SINGLE BASE-PAIR DNA SEQUENCE VARIATION DETECTION

RELATED APPLICATION DATA

This application claims the benefit of Provisional patent application Ser. No. 60/007,807, filed Nov. 30, 1995.

BACKGROUND OF THE INVENTION

1. Field of the Invention

The present invention relates to various molecular technologies for the detecton of DNA sequence variation. More specifically it provides a method to detect single base-pair variants in complex sources of DNA and DNA that is largely uncharacterized. Such sequence variants can be readily identified and mapped within in long segments (up to ~40 kb) of DNA amplified using the polymerase chain reaction. It provides a simple and sensitive approach to DNA sequence variation detection as well as a powerful and novel approach to genetics.

2. Description of Related Disclosures

Many methods have been developed to detect DNA sequence variation for the purpose of identifying genetic disease, genetic linkage studies, identity determination, etc. The most recent methods include RAPD (randomly amplified polymorphic DNA) analysis (Welsh and McClelland (1990), Nucleic Acids Res. 18:7213–7218), microsatellite length heterogenetity (U.S. Pat. No. 5,075,217) and an improved RNase mismatch detection method (Ambion, Inc.). For genetic mapping a variety of methods have been used the most popular of which include RFLP (restriction fragment length polymorphism) (Wyman and White (1980) PNAS 77:6754–6758), microsatellite length polymorphism (Nakamura et al (1987) Science 235:1616–1622; NIH/CEPH Collaborative Mapping Group (1992) Science 258:67–86) and AFLP (amplified linked polymorphism) (Vos et al (1996) Nucleic Acids Res. 23:4407–4414). For DNA fingerprinting commonly used methods include RFLP analysis (Giusti (1986) J. Forensic Sci. 31:409–417; Kanter et al (1986) J. Forensic Sci. 31:403–408), variable nucleotide tandem repeats (Jeffreys et al (1985) Nature 314:67–72) and microsatellites (Budowle et al (1991) Am. J. Hum. Genet. 48:137–144). For disease detection either inherited or aquired a large number of methods have been employed. These include DNA sequencing (Sanger et al (1981) Science 214:1201–1205), chemical cleavage (Cotton et al (1988) PNAS 85:4397–4401), RNase protection (Myers et al (1985) Science 230;1242–1246), single-stranded conformational polymorphism analysis (SSCP) (Orita et al (1989) PNAS 86:2766–2770), heteroduplex analysis (Keen et al (1991) Trends Genet. 7:5), heteroduplex analysis using bacteriophage resolvases (Mashal et al (1995) Nature Genetics 9:177–183; Youil et al (1995) PNAS 92:87–91), mutS binding to mismatched DNA (Su and Modrich (1986) PNAS 83:5057–5061; Ellis et al (1994) Nucleic Acids Res. 22:2710–2711; Jiricny et al (1988) Nucleic Acids Research 16:7843–7853; Wagner et al (1995) Nucleic Acids Research 23:3944–3948), denaturing gradient gel electrophoresis (Meyers et al (1987) Methods Enzymol 155:501–527), PCR clamping (Orum et al (1993) Nucleic Acids Res. 21:5332–5336), restriction fragment length polymorphisms (Orkin et al (1982) N Engl J Med 307:32–36), allele specific hybridization (Conner et al (1983) PNAS 80:278–282), hybridization to oligonucleotide probe arrays (Lipshutz et al (1995) BioTechniques 19:442–447), ligase chain reaction (Landergren et al (1988) Science 241:1072–1080, functional assays (Powell et al (1993) New Engl. J. Med. 329:1982–1987); Ishioka et al (1993) Nature Genetics 5:124–129); microsatellites (Sidransky et al (1992) Science 256:102–105; Mao et al (1994) PNAS 91:9871–9875; Brennan et al (1995), N Eng. J. Med. 332:429–435 and Hayashi et al (1995) N. Engl. J. Med. 345: 1257–1260; Boyle et al (1994) Am J. Surg. 168:429–432; Mao et al (1994) Cancer Res. 54:1634–1637); Sidransky et al (1991) Science 252:706–709), etc. For strain detection and breeding the follow methods are employed: RFLP analysis of PCR products (Meyer et al (1995) BioTechniques 19:632–639), RAPD (Hu and Quiros (1991) Plant Cell Rep. 10:505–511), and AFLP (Vos et al (1996) Nucleic Acids Res. 23:4407–4414).

While many methods exist to detect DNA sequence variation, they do not generally fullfill the criteria most useful for diagnostic and other purposes (Eng and Vijg (1997) Nat. Biotech. 15:422–426). Such criteria include 1) the ability to detect all types of point mutations, particularly since point mutations are the most common, 2) to not be severely restricted by the size of the DNA segment that can be examined in a particular assay, 3) to precisely map the site of variance, 4) to detect de novo mutations, 5) to be simple, rapid, and inexpensive. The present detection method overcomes these limitations and in addition provides added sensitivity for samples which are not pure.

Genetic mapping has been greatly advanced by the development and implementation of microsatellites. Yet even the use of these variants as markers has its limitations arising in part from their less than complete polymorphic information content (PIC) (Levitt et al (1994) Genomics 24:361–365). Microsatellites are also technically challenging to use since their resolution requires a sequencing gel and corrections software for polymerase stuttering artifacts. For complex disease factors the situation is more severe and in fact the present limitations of linkage mapping have been discussed by Risch (1996) in Science 273:1516–1517 and others (1997) in Science 275:1327–1330. Two important parameters are the number of markers used and the PIC of those markers. The power to detect linked loci can be increased either by the use of more markers or with the use of more fully informative markers (Risch (1990) Am. J. Hum. Genet. 46:242–253). The present detection method provides a means to generate genetic markers that potentially reach theoretical limits of PIC resulting in an increased power to detect linkage or a reduction in the number of assays and the number of false positives. A further benefit is a reduction in the number of relatives required for a given study.

The present detection method relies on the use of a familar enzyme or S1 nuclease. This enzyme has typically been used to degrade single-stranded DNA but can also cleave nicked double-stranded DNA or imperfect heteroduplexes containing loops or gaps (Vogt (1980) Methods Enzymol. 65:248–255). It has been commonly used in S1nuclease protection assays where imperfect DNA/DNA or DNA/RNA hybrids are assessed with respect to the length of the fragment protected from S1 digestion (Berk and Sharp (1977) Cell 12:721–723; Tanaka-Yamamoto et al (1989) Biochim. Biophys. Acta 1009: 151–155; Sugano et al (1993) 68:361–366; Ma et al (1994) Cardiovascular Res. 28:464–471; Limon et al. (1995) Leukemia 9:656–661). Paul Berg was the first to suggest the use of S1 nuclease for the detection of point mutations using ts mutants of SV40 which could be obtained in large quantities (Shenk et al (1975) PNAS 72:989–993). But it was clear that the activity was much less than that for other substrates as was later confirmed in studies using synthetic oligos which suggested even lower or negligible activity (Dodgson and Wells (1977)

16:2374–2379). When attempts were made to use the enzyme for the detection of mutations in human genomic DNA, these efforts failed (Myers et al (1985) 313:495–497) and in general the use of this enzyme was abandoned and replaced by other methods (Mashal et al (1995) 9:177–183). The present invention overcomes these earlier drawbacks with new conditions for optimal performance of the enzyme enabling the detection of single base-pair variants in complex sources of DNA such as human genomic DNA.

SUMMARY OF THE INVENTION

The present invention describes a molecular screen to detect single base-pair variations in DNA which are useful for genetic mapping, determining genetic identity, and identifying mutations associated with genetic disease, etc. The method overcomes many previous limitations in that it is not sequence dependent, can detect variants encompassed in relatively large segments of DNA, precisely maps the site of variance, detects de novo mutations, and is relatively easy to use. These features further provide a novel method for generating highly informative genetic markers that uses variation at the level of the individual to map loci in related individuals.

The method involves the isolation of DNA from cells followed by the amplification of a particular DNA segment of DNA using the polymerase chain reaction. The resulting amplified DNA segment is then denatured and renatured such that hybrids form between variant DNA strands. The hybrid duplex is then digested with S1 nuclease to generate fragments that are resolved by size separation methods such as slab gel electrophoresis (Shenk et al (1975) PNAS 72:989–993). The fragments are then detected by the Southern Blotting technique (Southern (1975) J. Mol. Biol. 98:503–517) using a nucleic acid detection probe, labeling of primers or amplified segment with sensitive tags like fluorescein, or sensitive staining of gels with reagents such as SYBR Green or silver.

BRIEF DESCRIPTION OF THE DRAWINGS

FIG. 1A–1B provide a diagramatic example of how S1 hybrid formation can be used to map genetic loci of interest. The diagrams only show the patterns expected for polymorphisms of interest, namely low frequency polymorphisms. In FIG. 1-A two sib-pairs are tested for three markers on three different chromosomes. The S1 digestion products essentially represent a partial digest since the enzyme digestion fails to go to completion. For each marker the products are indicated in each lane along with the full-length original PCR product. For a homozygous recessive condition the linked marker should produce identical banding patterns in both affected siblings as shown. In FIG. 1-B a dominant disorder is depicted showing the S1 hybrid banding patterns for several affected relatives with a single marker. While the banding pattern is not identicle for each affected sibling, a common digestion product is indicated, suggesting that they share a common parental allele that may be associated with the disorder.

DESCRIPTION OF THE PREFERRED EMBODIMENTS

The present method (FIG. 1) can be used for the rapid and sensitive detection of DNA sequence polymorphisms and mutations in a variety of cell types. In many instances the cells in question will be homogeneous, however, there may be occasions when the mutated genes are in only a fraction of the cells examined such as in a tumor biopsy. Theoretically, a limiting factor in the detection of mutations in populations of cells containing normal and mutant DNA is the background misincorporation by the polymerase used in the amplification step. Polymerases with a 3'–5' exonuclease editing activity have the lowest rate of misincorporation (Lundberg et al (1991) Gene 108:1–6) ~1.6×10-6/NT) such as that from Pyrococcus furiosus. Such misincorporation should occasionally result in background bands similar to those due to a true mutation in a particular sample (Krawczak et al (1989) Nucleic Acids Res. 17:2197–2201) but with much less intensity in routine applications. The lower limit of mutation detection for a 1.6 kb region should be around 1% of the cell population. For example, if one starts with 200 copies of genomic DNA (~60 ng)(100 cells) and the desired mutant is present as 1 copy (one allele in one cell) in a mixture (one mutant cell in 99 normal cells) then the ratio of mutant to background bands would be five to ten fold depending on whether or not misincorporation occurred during the first or second round of amplification. By starting with a greater quantity of DNA (300 ng) such background bands become insignificant (not detected by routine Southern Blot). If all the cells contain mutant or variant DNA then very large regions of DNA, limited by the PCR reaction itself, undesirable DNA sequence polymorphisms, and the kinetics of reassociation could theoretically be assayed for DNA mutations ~40 Kb, Barnes (1994) PNAS 91:2216–2220; Cheng et al (1994) PNAS 91:5695–5699, Cheng et al (1994) Nature Genet. 7:350–351; U.S. Pat. No. 5,436,149; Casna et al (1986) Nucleic Acids Res. 18:7285–7299).

Amplification of the DNA results in a high copy number of fragments and thus they can be denatured and rapidly renatured to allow heteroduplexes to form (Britten and Kohne (1968) Science 161: 529–540). Mismatches that occur in the heteroduplexes can then detected by S1 nuclease digestion. Digestion of single base-pair mismatches is the most difficult for the enzyme and the reaction does not go to completion (Shenk et al (1975) PNAS 72: 989–993). This is most likely the basis for the failure to detect digestion products by previous investigators when hybridizing a labeled DNA probe to cellular DNA (Myers et al (1985) Nature 313: 495–498). When using PCR amplified DNA, digestion with S1 yields sufficient quantities of each fragment to allow detection by Southern Blot analysis or other sensitive methods (fluorescent labeled primers or nucleotides, chemical staining such as silver, radio-labeled primers etc.). The optimal digestion conditions comprise determining the maximum concentration of S1 nuclease allowable that does not degrade the original starting product by nibbling away at the ends of double-stranded DNA molecules; single-stranded DNA (denatured genomic DNA) is a required carrier to minimize such nibbling activity. An additional factor is the possible need to optimize the enzyme to DNA ratio; for instance a is a prolific PCR product may need to be diluted in the presence of the same concentration of enzyme for increased specific activity.

When using a polymerase with a 3' to 5' editing function for reduced misincorporation, it is preferable to modify the primers with a 3' terminal phosphorothioate for fragments greater than 1.5 kb to prevent chew back of the primer by the polymerase (Skerra (1992) Nuc. Acids Res, 20:3551–3554). The amplification conditions should be optimized to yield a discrete band. Less than full length amplification products can be removed by quick spin column chromatography procedures (Mayo and Pham eds. "Nucleic Acid Purification with Chroma Spin Columns," CLONETECH, Inc.: Palo Alto, Calif.). Alternatively, the amplified product can be gel purified (Hensen, P. N. (1994) TIBS 19:388–389; Davis, L. G., Kuehl, W. M., Battey, J. F. eds. (1994) "Basic Methods in Molecular Biology," 2 ed., Appleton and Lange, Norwalk, Conn.). There are also several more recent gel purification devices such as Gelase™, Epicentre Technologies, Inc. (Bucan et al (1986) EMBO J. 5:2899–2905; SUPREC™ filter cartridges, PanVera, Inc.; and SpinBind™, FMC, Inc. If gel purification is used this typically removes both free primers as well as genomic DNA, thus a suitable amount of carrier DNA must be added back before performing S1 digestion. Fragments containing repetitive DNA must be gel purified to remove the interference caused by the genomic DNA.

While it is conceivable to amplify mRNA rather than DNA using RTPCR (Erlich, ed. (1992) "PCR Technology: Principles and Applications for DNA amplification,") reverse transcriptase has a much higher misincorporation rate, potentially limiting its utility. Even the use of a thermostable DNA polymerase for reverse transcription may not greatly improve the fidelity because the required manganese ions in the buffer increase the frequency of misincorporation (U.S. Pat. No. 5,310,652). This approach should be most feasible when the mutant cell population is largely homogenous as is the case with inherited disorders.

When the method results in small S1 digestion products, it is important to achieve optimal resolution of these fragments which is typically done by polyacrylamide gel electrophoresis. Improved methods in Southern Blotting procedures, namely, semi-dry electrophoretic blotting enable the transfer of DNA fragments from polyacrylamide gels as well as agarose to a nylon membrane for subsequent probing (Trnovsky (1992) Biotechniques 13:800–803). Agarose gels are generally simpler and faster to use and now many specialty grades and substitutes exist that provide acrylamide like resolution (NuSieve™ and MetaPhor™ agarose, FMC, Inc.; GelTwin™ and PCR Purity PlUS™, Baker, Inc.; Solbrig et al (1992) Strategies 5:43–44; Agarose SFR™, Amresco, Inc.). It is also possible to separate small DNA fragments by capillary gel electrophoresis (Schwartz et al (1992) Anal. Chem 64:1737–1740; Landers et al (1993) Bio/Techniques 14:98–111). Primers can also be labeled with fluorescent tags, radioactive phosphate, or chemiluminescent linkers such as psoralen biotin (Giusti and Adriano (1993) PCR Methods and Applications. 2:223–227; Berkner and Folk (1977) J. Biol. Chem. 252:3176–3182; U.S. Pat. No. 4,599,303) for convenient detection in slab gels using an image scanner (Molecular Dynamics). SYBR Green™ (Molecular Probes) or silver staining (especially when denatured) of gels may also permit adequate detection for certain applications.

Natural DNA sequence variation in humans occurs at a low but detectable level. The estimated mean extent of heterozygosity is on the order of 0.2 percent (Hofker et al (1986) Am. J. Hum. Genet. 39:438–451; Springer (1988) Ph.D. Dissertation, Univ. of California, Riverside; Rowen et al (1996) Science 272:1755–1762). The frequency of any minor allele varies with about 50% being more frequent ranging from 0.2 to 0.45 while the remaining 50% are less frequent ranging from 0.03 to 0.15. Invertebrates appear to exhibit a greater degree of heterozygosity (Kreitman (1983) Nature 304:412–417). To distinguish DNA polymorphisms from mutant DNA sequences associated with a disease state it is necessary to run a control DNA sample from the same individual isolated from non-disease state tissue. Buccal cells from the cheek or blood cells are typically used as control samples. Alternatively, mutations can be mapped to known sites associated with the disease state.

The present invention may have considerable utility for genetic research because it allows for the rapid and simple detection of DNA sequence polymorphisms anywhere in the genome. Since such polymorphisms occur frequently it is possible to generate markers at a high resolution, higher than available by microsatellites and in a broader range of organisms (Livak et al (1995) Nature Genet. 9:341–342; Hamada et al (1982) PNAS 79:6465– 6469). Such markers can be used for mapping hemizygous genomic DNA deletions found in tumor cells (loss of heterozygosity) and linkage disequilibrium mapping in the vicinity of a known genetic marker of the disease locus (Zenklusen et al (1994) PNAS 91:12155–12158; Lucassen et al(1993) Nature Genet. 4:305–310) as well as for diagnostic tools in genetic counseling of inherited disorders particularly, where no other pre-established marker is available (Roberts et al (1989) Nucleic Acids Res. 17:5961–5971). They may also be useful for forensic or human DNA fingerprinting.

The detection method also potentially provides a useful means of mapping disease or other loci, reducing the number of families and genotypes one needs to examine several fold (Bodmer, W F (1986) Cold Spring Harbor Quant. Symp. 51:1–13). This is because the method provides a means to generate highly informative DNA markers that use variation at the level of the individual to map loci in related individuals (e.g. affected siblings) (Risch (1990) Am. J. Hum. Genet. I, II, & III 46:222–253). Such variation in the population should represent low frequency alleles making the chance observation of sharing those alleles in siblings unlikely unless inherited from a common parent or other relative. In this regard, it is necessary to prescreen markers for more common polymorphisms to eliminate or reduce such interference in the analysis. The novel approach of genetic mapping reduces the number of additional relatives needed to be typed for affected pairs to determine the phase or heterozygosity of particular alleles; such as the parents for sib-pairs. The number of families required is also reduced by the increased efficiency of the markers.

The method can also be applied to the identification of a disease locus by detecting mutations in potential protein coding sequences determined by homology to cDNA clones, exon trapping (Auch and Reth (1990) Nucleic Acids Res. 18:6743–6744), genomic sequencing, or other methods. Other detection methods show either a dependence on the size of the DNA fragment analyzed (muts, SSCP, Rnase cleavage) or exhibit high background (bacteriophage resolvases; Rnase cleavage, Ambion), or show sequence specificity (Rnase cleavage has a preference for transversions over transition mutations while transitions are much more prevalent in hereditary disorders) or do not cleave at the site of the mismatch (bacteriophage resolvases, RNase A). In contrast, with S1, there does not appear to be any cleavage sequence specificity based on the enzyme's mechanism of action (Shenk et al (1975) PNAS 72:989–993). Using synthetic oligos digestion has been observed at dA.dG and dG.dG mismatches (Dodgson and Wells (1977) Biochemistry 16:2374–2379). In addition, $S_1$ nuclease has been used extensively in $S_1$ nuclease mapping of RNAs (Berk and Sharp (1977) Cell 12:721–723).

EXPERIMENTAL

EXAMPLE I

Method to Detect Mutant Oncogenes

General Procedure

Cells in suspension should be concentrated by centrifugation for subsequent DNA isolation. Rapid methods for DNA isolation exist that do not require organic solvents (Grimberg et al (1989) Nucleic Acids Res. 17:8390; Willis et al (1990) Bio/Techniques 9:92–9; InstaGene Matrix, Bio-Rad). DNAzol™ (Molecular Research Center) is a strong denaturant containing a guanidine-detergent based lysing solution which hydrolizes RNA and allows the selective precipitation of DNA with ethanol (Ausubel et al (1990) in "Current Protocols in molecular Biology," vol. 2, p. A.1.5: John Wiley & Sons, New York). To isolate DNA from whole blood (100 ul or more) it is best to first isolate nuclei by lysing the cells with triton X-100 in the presence of sucrose (Grimberg et al (1989) Nucleic Acids Res. 17:8390). Following pelleting of cells or nuclei in a microcentrifuge, the sample is resuspended in the guanidine-detergent by gentle pipeting up and down. Tissue biopsies must be homogenized in DNAzol using a homogenizer whereas cell monolayers can be lysed by simply pipeting the solution onto the culture plate.

Hot spots for mutations in the p53 gene occur in exons 5–8. The detection of mutations in this region is complicated by the presence of Alu sequences in intron six. This can be overcome by using two PCR primer pairs SEQ. ID. NOS. 1–4 that generate two smaller PCR products which avoid the repeat or by purifying a larger product (primers SEQ. ID. NOS. 1 and 4) containing the repeat from genomic DNA by gel purification (note prior to $S_1$ treatment a suitable amount of carrier must be added to replace the lost genomic DNA). The primers should be modified at the 3' terminus with phosphorothioate when using Pfu. The two smaller products generated by PCR encompass exons 5 and 6 as well as 7 and 8 yielding products 448 bp and 618 bp in length, respectively. Alternatively, by avoiding the middle primers a 1537 bp product is generated.

The PCR reaction is carried out using standard conditions (Saiki et al (1985) Science 37:170–172; Henry Erlich ed. (1992) "PCR Technology: Principles and Applications for DNA Amplification," W. H. Freeman and Company, New York) optimized for Pfu (Scott et al (1994) Strategies 7:62–63; Stratagene). For instance, a 100 ul reaction containing 250 ng of genomic DNA is used (the higher concentration minimizes the background associated with misincorporation). The final concentration of primers should be 50 pmol of each primer per reaction volume or 0.3 to 1 uM. Pfu is a high fidelity polymerase that gives optimal performance in a low salt buffer (2.5 units per reaction): 40 uM each dNTP, 10 mM KCL, 10 mM ammonium sulfate, 20 mM Tris-CL (pH 8.0), 2 mM magnesium sulfate, 0.1% triton, 100 ug/ml bovine serum albumin. It is necessary to use a hot start procedure where the enzyme is added last to prevent mispriming. This can be done manually or with the use of wax beads. The cycling protocol used for the larger product with a Perkin Elmer 9600 cycler is as follows: hold 5 min. 94° C. (then add polymerase), cycle 30 times at 94° C. for 15 sec, 67° C. for 15 sec, and 72° C. for 3 min, followed by a final extension of 7 min at 72° C.

The PCR reaction is then treated to remove free primers, free oligonucleotides, and less than full length reaction products using Clontech Chroma Spin™ –200, 400, or 1000 depending on the product size. Alternatively, to remove repetitive DNA as well as other unwanted components the PCR product can be run on an low melting agarose gel and purified using SpinBind™ extraction units (FMC); SUPREC™ filter cartriges (PanVera); or Gelase™ (Epicentre Technologies). The sample should be resuspended in a small volume ~20 ul to facilitate renaturation of the DNA.

To generate heteroduplexes the samples must be denatured and renatured before digesting with S1 nuclease. At least one sample should not be denatured to serve as a control for S1 nuclease artifacts and to demonstrate the dependency of the assay on the formation of a heteroduplex. Denaturation is initiated by heating in water at 94° C. for several minutes. Afterwhich, the sample is cooled to 68° C. and the S1 nuclease buffer containing 280 mM salt is added to facilitate reannealing. This is best accomplished by performing the denaturation and renaturation steps in the PCR machine to avoid loss in volume due to evaporation. Most of the DNA should reanneal in 60 min. assuming a good yield of amplified product in a final volume of 20 ul. The sample is then transferred to 37° C. followed by the addition of S1 nuclease (~1 unit per ul) for 30 min. The genomic DNA in the sample which will denature but not renature during the assay conditions serves as a carrier or buffer for the enzyme. The enzyme can then be removed using StrataClean™ resin (Stratagene). As a quality control measure a portion of a control sample should be diluted to test for the sensitivity of the assay.

Mix samples with loading buffer and run on an agarose or acrylamide gel. For small fragments, improved resolution of agarose gels can be obtained using agarose additives or substitutes that provide acrylamide like resolution (NuSieve™, FMC or GelTwin™, Baker, Inc.). The gel is then transferred to a nylon membrane for Southern analysis. A slightly positive membrane (BIODYNE™ Plus, Pall; Nytron Plus™, Schleicher & Schuell) is optimal for retaining small fragments (background can vary with different brands).

Once the DNA has been transferred to the nylon membrane, the DNA should be fixed by baking for 1 hr. at 75°–80° C. or by UV irradiation (Church and Gilbert (1984) PNAS 81:1991–1995). The blot is then probed using non-radioactive detection methods with cDNA sequences or end specific probes to localize the mutation to the 5' or 3' end of the fragment (Holtke et al (1992) Bio/Techniques 12:104–113; Gebeyehu et al (1987) Nuc. Acids Res. 15:4513–4534; Nguyen et al (1992) Bio/Techniques 13:116–123; Luehrsen et al (1987) Bio/Techniques 5:660). For example, a recombinant SP6/T7 plasmid containing a p53 cDNA insert (Oncogene) can be used to synthesize p53 RNA sequences in vitro (Wolf et al (1985) Mol. Cell. Biol. 5:1887–1893). If the RNA is labeled using biotin-21-UTP (Clonetech) (Luehrsen, et al. (1987) Bio/Techniques 5:660–665) then it can be visualized by chemiluminescence. In particular, the RNA probe is detected using strepavidin linked to alkaline phosphate (Keller and Manak eds. (1993) "DNA Probes," 2nd ed., pgs. 483–523: Stockton Press, New York; GIBCO/BRL). Then a chemiluminescent substrate is used (CSPD, U.S. Pat. No. 5,112,960, Boehringer Mannheim). The lumigen should be sprayed on to avoid high background. The gel can then be exposed to X-ray (X-OMAT AR, Kodak) or Polaroid film for rapid detection.

When using RNA probes, the hybridization step must be carried out with formamide to reduce the temperature required for annealing. RNA/DNA hybrids have a Tm that is 10°–15° C. higher than DNA/DNA hybrids (Sambrook et al (1989) Molecular Cloning: A Laboratory Manual, 2nd ed.: Cold Spring Harbor Laboratory, Cold Spring Harbor, New York). (Optimal hybridization is 25° C. below the Tm). The amount of probe required is 100 to 500 ng/ml. Hybridization Solution: 5XSSC, 50% formamide, 0.1% N-lauroyl-sarcosine, 0.02% SDS, 5% blocking reagent (casein fraction of dried milk), 100 ug/ml of denatured salmon sperm DNA. Carry out the pre-hybridization step in 20 ml solution containing formamide per 100 $cm^2$ filter at 50° C. for 1 hr. Then replace the prehyb. solution with 2.5 ml hybridization solution containing probe per $cm^2$ filter. Incubate filters for at least 6 hr. at appropriate temp. Higher RNA concentrations can be used to shorten the hybridization time to 2 hr. The filters are then washed twice for 5 min. at room temp. with at least 50 ml of 2XSSC, 0.1% SDS and then twice for 15 min. at 68° C. with 0.1XSSC, 0.1% SDS. Quantitation: This can be obtained by reading the developed film with a densitometer or image scanner (Molecular Dynamics). A rough estimate can also be obtained using known quantities of control samples for comparison. When looking at the bands it is important to remember that S1 nuclease does not completely digest single basepair mismatches. At a low ratio of mutant to normal cells the apparent number of mutant fragments increases two fold, since each strand of the original mutant homoduplex pairs with a normal DNA strand.

Verification: The detection of a variant does not in and of itself prove that the p53 gene is inactive; it is possible that the variant maps to an intron polymorphic site rather than a codon mutation. The sample should be compared relative to normal cells to eliminate the possibility of an unkown polymorphism.

Specific Results

To establish the experimental conditions DNA from SW40 colon carcinoma cells (Clontech) was used which contains a homozygous mutation at amino acid 273 of the p53 protein resulting in a change from CGT to CAT (Arg to His). When mutant DNA is mixed with normal DNA in a heteroduplex this creates a G/T and A/C mismatch. Initially PCR amplification using Pfu with primers to generate the 1537 bp product resulted in a much smaller than expected product ~600 bp that could be detected by EtBr staining of an agarose gel. Elevating the annealing temperature from 62° to 67° C. increased the production of the larger product and no smaller product was seen by EtBr stain. When a Southern Blot (routine capillary action transfer) was performed, the larger product was detected as well as a small amount of the smaller product. Several less than full-length bands were also detected by Southern Blot in trace amounts indicating polymerase pausing or premature termination. These could be removed by using Chroma-Spin™ 1000 columns to produce a clean background.

Too much S1 enzyme produces a smear, with the concentration of the enzyme as well as the ratio of enzyme to PCR product being critical. To optimize digestion of the PCR product the sample may need to be diluted (~2 fold) rather than with the addition of more enzyme. It is also important that the genomic DNA is completely denatured, otherwise it will reanneal and not protect the fragment from S1 degradation. A clean background was observed when the 1537 bp product was not denatured and digested with S1 nuclease (a useful control for S1 artifacts). In contrast when the fragment was denatured and renatured several fuzzy bands were detected ~600 –1200 bp. These can be attributed to hybridization of genomic DNA with the repetitive DNA in the fragment. Only when a PCR fragment from normal DNA was denatured and reannealed with mutant DNA to form heteroduplexes was an additional fragment observed corresponding to the digestion of the single base pair mismatch by S1 nuclease (1423 bp).

EXAMPLE II (Theoretical)

Method to map disease loci to specific chromosomal regions.

The first step in mapping a particular genetic disease is to assign the defective trait to a specific chromosome. This is typically accomplished by examining affected pairs such as siblings in a given family for shared alleles of a given chromosome. While RFLPs and other single nucleotide polymorphisms have been used as chromosomal markers (Noguchi, M. et al (1993) Cell:73:147–157, the low heterozygosity of these markers restricts their general utility. In previous studies polymorphisms present at high frequencies were favored since they provided the greatest number of informative inheritance patterns in clinical samples. In addition, the assays focused on very small segments of DNA ranging from 4 bp to ~200 bp. However, if one considers a much larger segment of DNA (~2 kb) that encompasses many low frequency polymorphisms, then even if one such polymorphism is present in only 10% of all individuals, the chances are still high that each individual will possess at least one low frequency polymorphism from the pool of possible polymorphisms for that region of DNA. These minor or unique variants can be used to discriminate individual parental alleles among siblings.

The detection of minor polymorphisms using S1 hybrid analysis enables the ready distinction of all four possible maternal and paternal allelic combinations in the affected individual. For a homozygous recessive condition, this is achieved by analyzing specific regions of the genome (i.e. PCR products) that contain on average at least three low frequency polymorphisms located on three of four parental alleles (only two are required to discriminate alleles but with three the number of uninformative assays is reduced). (For a dominant trait one needs at least four low frequency polymorphisms, one for each parental allele). The number of polymorphisms can be controlled by the length of the fragment examined with an expectation of two polymorphisms per kb. The frequencies (q) of the polymorphisms used, corresponding to an allele in the population, should be low making their chance observation ($q^2$) in two individuals unlikely. More frequent polymorphisms should be noted or avoided and used only as supplemental information. Thus each combination of any two parental alleles should reveal a fairly unique S1 hybrid digestion banding pattern for that pair.

To adequately mark each of the 22 autosomes one should develop at least ~140 markers. A marker should be placed at the tip of each telomere and then spaced at intervals of every ~30 cM. Thus, each mutant locus should be bounded by a marker on both sides. Because of recombination events there is the possibility that one or both of the proximal and distal markers will be lost in the affected siblings examined. The maximum possibility that a given mutant locus may be missed because of such recombination events occurs when the mutation is located half-way between the two markers; even so the when considering a recessive trait the chance of not detecting linkage is low (<20%). By repeating the analysis on additional sib-pairs one can increase the power to detect linkage.

In the first step all markers should be scored for both affected siblings in a given family (FIG. 1). The random probability that any two siblings will inherit the same maternal and paternal chromosomes is 0.25 (the random probability of sharing one chromosome is 0.50 as in the case of a dominant condition). Once a marker has been observed to be shared by a pair of siblings that marker should be examined in several additional affected sib-pairs to establish linkage to the disease locus (Risch (1990) Am. J. of Hum. Genet. II 46:229–241).

Unaffected siblings can be examined as long as the trait is completely penetrant to eliminate other possibilities. If several siblings are available the power of the technique increases $(0.75)^N$, where N=the number of siblings.

Once a candidate chromosome marker has been identified additional markers may help to further localize the locus since recombination events will separate specific maternal and paternal chromosome pairs. Alternatively, allele specific markers can be identified by examining previous generations. These can then be used to identify recombinants in affected individuals to further delineate a particular locus by pinpointing sites of recombination.

To generate markers it is possible to start with known sequenced tagged sites (Chumakov et al (1995) Nature 377:175–297; Gemmill et al (1995) Nature 377:299–319; Krauter et al (1995) 4377:321–333; Collins et al (1995)

Nature 377:367–379; CHLC et al (1994) Science 265:2049–2070) (http://www-genome.wi.mit.edu/). Markers can then be generated from sequenced tagged sites using the technique of inverse PCR (Ochman et al (1988) Genetics 120:621–623; Triglia et al (1988) Nucleic Acids Res. 16:8186) or panhandle PCR (U.S. Pat. No. 5,470,722). The fragment should preferably be free of repetitive DNA including microsatellites and contain as few frequent polymorphisms as possible to simplify the analysis. Candidate fragments should be further prescreened by examining 50–100 people to gain information about allele frequencies in specific populations (Caucasians, etc.).

What is claimed is:

1. A method for detecting and mapping single base-pair genetic DNA variants in complex or natural sources of DNA comprising:

1) amplifying one or more specific segments of DNA via polymerase chain reaction involving two oligonucleotide primers complementary to the ends of the segments of DNA, 2) denaturing the amplified DNA so that both strands of DNA are completely separated, 3) renaturing the denatured DNA to form heteroduplexes containing DNA mismatches, 4) digesting the mismatched DNA heteroduplexes with S1 nuclease so that a non-base-paired region is cleaved to produce DNA fragments whose lengths correspond to the site of a single base-pair mismatch, and 5) detecting S1 nuclease digestion products via gel electrophoresis and southern blotting with a labeled complimentary nucleic acid probe.

2. The method of claim 1 wherein the detecting comprises labeling the amplified DNA with a labeled primer or nucleotide prior to size separation of DNA fragments by capillary or slab gel electrophoresis.

3. The method of claim 1 wherein the detecting comprises electrophoresis and chemical staining of gels with silver, fluorescent or chromogenic compounds.

4. The method of claim 1 wherein the segments of DNA for amplification are source DNAs which comprise a mixture of cDNAs prepared by reverse transcription of cellular RNA.

5. The method of claim 1 wherein the segments of DNA for amplification are source DNAs which are genomic DNA.

6. The method of claim 1 wherein the segments of DNA for amplification are source DNAs which are mitochondrial or chloroplast DNA.

7. The method of claim 1 wherein the amplification of the segments of DNA is performed with more than one primer pair so that more than one DNA segment is amplified.

8. The method of claim 1 further comprising the detection of genetic abnormalities associated with disease states in individuals wherein the segments of DNA to be amplified are either disease or non-disease source DNA and the detection of genetic abnormalities is via comparison of the amplified disease source DNA and the amplified non-disease source DNA.

9. The method of claim 1 further comprising the detection of heritable defects, wherein the segments of DNA to be amplified are from either test individual or control individual source DNA and the detection of heritable defects is via comparison of the amplified test individual source DNA and the control individual source DNA.

10. The method of claim 1 further comprising distinguishing viral and bacterial strains from one another.

11. A method for genome mapping comprising:

1) amplifying a portion of a genetically mapped or tagged marker region via polymerase chain reaction, 2) amplifying a region corresponding to the marker region from a population of individuals, 3) denaturing the amplified DNA from steps 1) and 2), 4) renaturing the denatured DNA to form heteroduplexes, 5) digesting the heteroduplexes with S1 nuclease, 6) detecting single base-pair or bi-allelic polymorphisms, 7) determining the size of DNA segments which give said polymorphisms at a frequency of less than 20%, and 8) distinguishing between parental and precessive alleles in affected individuals by measuring nuclease digestion products that result from said polymorphisms.

12. The method of claim 11 wherein the affected individuals are sib-pairs.

13. The method of claim 11 wherein the affected individuals are cousins, grandfather-grandchild pairs, uncle-nephew pairs or half-sibs.

14. The method of claim 11 wherein the polymorphisms are correlated with a disease state in a collection of non-related affected individuals.

15. The method of claim 11 wherein single base-pair polymorphisms are detected by chemical mismatch cleavage, DNA sequencing, enzymatic cleavage or oligonucleotide hybridization.

* * * * *

UNITED STATES PATENT AND TRADEMARK OFFICE

CERTIFICATE OF CORRECTION

PATENT NO. : 5,811,239

DA'ED : September 22,1998

INVENTOR(S) : Elizabeth Gay Frayne

It is certified that error appears in the above-identified patent and that said Letters Patent is hereby corrected as shown below:

Col. 2, line 6, change 'Genecheck' to ...Genecheck,...
Col. 2, line 6, change 'Dependence' to ....Dependence of...
Col. 2, line 7, change 'Muts' to ...MutS, 400...
Col. 2, line 7, change 'Horestooth Fort Collins' to ...Horestooth, Fort Collins...
Col. 2, line 13, change 'Autosomes' to ...Autosomes"...'
Col. 2, line 16, change 'BT' to ...T...
Col. 2, line 21, change 'Risch' to ...Risch"...
Col. 2, line 22, change 'Marker of' to ...Marker Polymorphism on...
Col. 2, line 27, change 'Merikangas' to ...Merikangas, "Genetic Analysis of Complex Diseases"..."
Col. 2, line 28, delete 'Genetic Analysis of Complex Diseases'.
Col. 2, line 32, change 'Polymorphisms' to ...Polymorphisms"...
Col. 2, line 35, change 'Research Genetics' to ...Research Genetics,...
Col. 2, line 38, change 'SI' to ...S1...
Col. 2, line 39, change 'Htbrids' to ...Hybrids...

UNITED STATES PATENT AND TRADEMARK OFFICE

CERTIFICATE OF CORRECTION

PATENT NO. : 5,811,239

DATED : September 22,1998

INVENTOR(S) : Elizabeth Gay Frayne

It is certified that error appears in the above-identified patent and that said Letters Patent is hereby corrected as shown below:

Col. 1, line 28, change 'Webor' to... Weber...
Col. 1, line 48, change 'et al Biochemical' to ...et al., "Biochemical...
Col. 1, line 49, delete 'PNAS'.
Col. 1, line 50, change 'SU40' to ...SV40...
Col. 1, line 51, change 'Dodgson & Wells Action' to ...Dodgson & Wells, Action...
Col. 1 , line 53, change 'Sequence Biochemistry' to Sequence" Biochemistry...
Col. 1, line 54, change 'Meyers et al Detection' to ...Meyers et al., "Detection...
Col. 1, line 55, change 'DNA' to ...DNA"...
Col. 1, line 57, change 'Resoluases' to ...Resolvases...
Col. 2, line 1, change 'Promis' to ...Promise"...
Col. 2, line 2, delete 'in'.

Signed and Sealed this

Eighth Day of June, 1999

Attest:

Q. TODD DICKINSON

*Attesting Officer* *Acting Commissioner of Patents and Trademarks*